United States Patent [19]

Mount et al.

[11] 4,111,963

[45] Sep. 5, 1978

[54] METHOD FOR PREPARING MALEIC ANHYDRIDE

[75] Inventors: Ramon A. Mount; Harold Raffelson, both of St. Louis, Mo.

[73] Assignee: Monsanto Company, St. Louis, Mo.

[21] Appl. No.: 640,121

[22] Filed: Dec. 12, 1975

Related U.S. Application Data

[60] Continuation of Ser. No. 471,117, May 17, 1975, abandoned, which is a division of Ser. No. 330,354, Feb. 7, 1973.

[51] Int. Cl.$^2$ ............................................. C07D 307/60
[52] U.S. Cl. .................................. 260/346.75; 252/437
[58] Field of Search ................................ 260/346.8 A

[56] References Cited

U.S. PATENT DOCUMENTS

| | | | |
|---|---|---|---|
| 3,296,282 | 1/1967 | Kerr | 260/346.8 A |
| 3,864,280 | 2/1975 | Schneider | 260/346.8 |
| 3,915,892 | 10/1975 | Harrison | 260/346.8 |
| 3,985,775 | 10/1976 | Harrison | 260/346.8 A |
| 4,017,521 | 4/1977 | Schneider | 260/346.8 A |

*Primary Examiner*—Henry R. Jiles
*Assistant Examiner*—Bernard Dentz
*Attorney, Agent, or Firm*—J. C. Logomasini; P. L. Passley; S. M. Targer

[57] ABSTRACT

The productivity of phosphorus-vanadium-oxygen catalysts useful for converting saturated hydrocarbons containing from 4 to 10 carbon atoms to maleic anhydride can be increased by the order of preparatory steps used to prepare such catalysts. Phosphorus-vanadium-oxygen catalysts are prepared by mixing phosphorus and vanadium compounds to form precursors, shaping precursors and then calcining the precursors to form the catalysts. The catalysts are particularly beneficial for the conversion of butane to maleic anhydride.

3 Claims, No Drawings

METHOD FOR PREPARING MALEIC ANHYDRIDE

This is a continuation, of application Ser. No. 471,117, filed May 17, 1974, now abandoned, which is a division application of pending prior application Ser. No. 330,354 filed Feb. 7, 1973.

BACKGROUND OF THE INVENTION

This invention relates to a method for preparing catalysts useful in the manufacture of dicarboxylic acid anhydrides by the oxidation of hydrocarbons. More particularly, it is directed to the preparation of catalysts suitable for producing maleic anhydride from saturated hydrocarbons in higher yields than heretofore possible.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these needs.

The prior art discloses a number of catalysts used in the conversion of organic feed stocks to maleic anhydride. As an example, U.S. Pat. No. 2,773,836 discloses phosphorus-vanadium-oxygen catalysts for the conversion of olefins to maleic anhydride. The catalysts had a weight ratio of $V_2O_5$ to $P_2O_5$ of 3:2 to 1:2, and were prepared by adding a vanadium compound to phosphoric acid, optionally adding a carrier to the solution, removing the excess liquid by evaporation, drying the remaining material at 200° – 400° F., grinding the resulting solids, and heating to 700° –1100° F. for several hours. U.S. Pat. No. 3,156,707 also discloses a similar method for preparing phosphorus-vanadium-oxygen catalysts for the conversion of olefins to maleic anhydride. The vanadium in these catalysts was reduced to an average valence in the range of 2.5 to 4.6 using an acid such as hydrochloric acid or oxalic acid during the preparatory steps.

Of particular interest is U.S. Pat. No. 3,293,268 which teaches a process of oxidizing saturated aliphatic hydrocarbons to maleic anhydride under controlled temperature conditions and in the presence of phosphorus-vanadium-oxygen catalysts. One method taught in that patent for preparing catalysts comprised reacting phosphoric acid with a vanadium compound in aqueous hydrochloric acid solution, recovering the remaining solids by evaporating the solution to dryness, and then heating the solids to 300° to 500° C. The resulting catalysts were ground to pass a 20 mesh screen and pelleted to form tablets. The tablets were then charged to a fixed catalyst bed in a test reactor at room temperature and the reactor heated for 16 hours. Thereafter, a 0.5 volumne percent butane in air mixture was passed through the catalyst in a fixed tube reactor at temperatures above 400° C to form maleic anhydride.

Although yields in excess of 35 weight percent were reported in U.S. Pat. No. 3,293,268 when using low butane concentrations in air, these yields were achieved only at temperatures between 500° C and 600° C. At temperatures below about 500° C, the yields of maleic anhydride were reported to be less than about 20 weight percent. On the other hand, the catalysts of the present invention can convert butane to maleic anhydride in significant yields at temperatures as low as 350° C. Since it is well known to those skilled in the art that the more active catalysts can convert hydrocarbons to maleic anhydride at lower operating temperatures, the improved yields at lower operating temperatures that are achieved using the present catalysts show that the present catalysts are far superior to the prior art catalysts.

SUMMARY OF THE INVENTION

It is an object of this invention to provide improved phosphorus-vanadium-oxygen catalysts. It is another object to provide a process for preparing improved phosphorus-vanadium-oxygen catalysts suitable for converting saturated hydrocarbons to maleic anhydride. It is another object to provide improved phosphorus-vanadium-oxygen catalysts particularly suitable for converting butane to maleic anhydride.

These and other objects are achieved by the process disclosed herein to provide a catalyst comprising phosphorus, vanadium and oxygen, the phosphorus to vanadium ratio being in the range of about 1:2 to about 2:1 and the catalyst having a porosity of at least about 35 percent as determined by the porosity test hereinafter described, and wherein a substantial amount of the vanadium is in the tetravalent state.

For the purposes of this invention, the term "catalytic activity" means the ability to convert a particular feed stock, such as butane, at a particular temperature to other compounds. The term "selectivity" means the ratio of the moles of maleic anhydride obtained to the moles of hydrocarbon reacted. The term "yield" means the ratio of the moles of maleic anhydride obtained to the moles of feed introduced into the reaction. The term "space velocity" means the hourly volume of gaseous feed expressed in cubic centimeters (cc) at 60° F and standard atmospheric pressure, divided by the catalyst bulk volume expressed in cubic centimeters (cc), the term expressed as cc/cc/hour.

The catalysts of this invention are particularly useful for the conversion of butane to maleic anhydride. These catalysts have characteristics which distinguish them from prior art catalysts used in the manufacture of dicarboxylic acid anhydrides, and the methods by which the present catalysts are prepared cause these distinguishing characteristics. Details of the catalyst preparation, their distinguishing characteristics and means by which such characteristics can be determined and the use of the present catalysts to convert saturated hydrocarbons to maleic anhydride are hereinafter described.

PREPARATION OF THE CATALYSTS

Broadly described, the catalysts of this invention are prepared by contacting vanadium and phosphorus compounds under conditions which will provide a substantial amount of vanadium in the tetravalent state to form a catalyst precursors, recovering the catalyst precursors, forming the catalyst precursors into structures for use in a maleic anhydride reactor, and calcining the structured catalyst precursors to form the catalysts.

The vanadium compounds useful as a source of vanadium in the catalyst precursors are those known to the art. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

As a source of phosphorus in the catalyst precursors useful phosphorus compounds are also those known to the art. Suitable phosphorus compounds include: phosphoric acids, such as metaphosphoric acid, orthophosphoric acid, triphosphoric acid, pyrophosphoric acid, phosphorous acid and the like; phosphorus oxides such as phosphorus pentoxide and the like; phosphorus halides such as phosphorus oxyiodide, phosphorus pentachloride, phosphorus oxybromide and the like; and organophosphorus compounds such as ethyl phosphate, methyl phosphate and the like. However, phosphoric acids, such as orthophosphoric acid, and phosphorus pentoxide are preferred.

To prepare the catalyst precursors, a vanadium compound is heated with a phosphorus compound in an acid solution to dissolve the starting materials. A reducing agent is used to reduce any pentavalent vanadium to tetravalent vanadium and to maintain vanadium in the tetravalent state. As is well known to those skilled in the art, hydrogen halide acid or oxalic acid solutions, which are mild reducing agents, can serve not only as the acid but also as the reducing agent for the pentavalent vanadium. Hydrochloric acid is preferred. The acid solution containing phosphorus compound and vanadium compound are heated until a blue solution is obtained, indicating that a substantial amount, i.e. greater than 50 atom percent, of the vanadium is in the tetravalent state. The amount of time required to dissolve the phosphorus and vanadium compounds and to reduce a substantial amount of the vanadium to the tetravalent state to form the catalyst precursors varies from batch to batch, depending upon the compounds used as starting materials and the temperature at which the compounds are heated. However, as will occur to those skilled in the art, an aliquot of the solution can be analyzed to insure that most of the vanadium is in the tetravalent state.

Although any number of phosphorus compounds and vanadium compounds can be used to form the phosphorus-vanadium-oxygen precursor, the atom ratio of phosphorus to vanadium in the precursor is important since it controls the phosphorus to vanadium atom ratio in the final catalyst. When phosphorus-vanadium-oxygen precursors contain a phosphorus to vanadium atom ratio below about 1:2 or above about 2:1, the yield of maleic anhydride using the catalysts of this invention is so low that it is not of commercial significance. It is preferred that phosphorus-vanadium-oxygen precursors have a phosphorus to vanadium atom ratio in the range of about 1:1 to about 1.5:1, and more preferably to have a phosphorus to vanadium atom ratio to about 1:1 to about 1.2:1, say about 1.1:1.

After the vanadium and phosphorus compounds are mixed and substantially all the vanadium has been reduced to the tetravalent state, it is necessary to remove most of the water in order to recover the phosphorus-vanadium-oxygen precursors. Techniques for recovering the phosphorus-vanadium-oxygen precursors from solution are well known to those skilled in the art. The precursors can be deposited on a carrier, such as alumina or titania, from the aqueous solution, or the precursors can be dried by gentle heating to recover the solid phosphorus-vanadium-oxygen precursors from solution.

After the phosphorus-vanadium-oxygen precursors are recovered from solution, they are then formed into structures suitable for use in a maleic anhydride reactor. Techniques for forming appropriate structures from the precursors for use in a fluidized bed reactor or in a fixed tube heat exchanger type reactor are well known to those skilled in the art. For example, the precursors can be structured for use in a fluidized bed reactor by depositing the phosphorus-vanadium-oxygen precursors from solution on a carrier such as titania or alumina. Alternatively, the dried precursors can be comminuted for use in a fluidized bed reactor. On the other hand, the precursors can be structured for use in a fixed tube reactor by prilling or tabletting the precursors.

In a preferred embodiment, the aqueous solution containing the phosphorus-vanadium-oxygen precursor is evaporated to apparent dryness. Then, from about 10 to about 40 weight percent water is added to the precursor to form a putty. Alternatively, only so much of the water from the aqueous solution of phosphorus-vanadium-oxygen precursor is removed as is necessary to form a viscous putty. The amount of water in the putty is not critical provided that there is sufficient water to permit forming into a suitable structure as by extrusion or pelleting, but not so much water as to cause the wet mixture to slump after it is formed. A putty containing less than about 10 weight percent water is difficult to extrude whereas a putty containing greater than about 40 weight percent water will normally slump and not hold its shape. However, it should be noted that various additives, such as a gelling agent or a lubricant, can be added to the putty That can change this ratio, as will occur to those skilled in the art. The putty of precursor and water is then structured by extruding the putty through a die, drying the extrudate and dividing extrudate into pellets or tablets. Alternatively, the extrudate can be divided into pellets before drying and this latter procedure is preferred.

It is critical in the process of the present invention to calcine the phosphorus-vanadium-oxygen precursors after they are formed into the structures which will be used in the maleic anhydride reactor. After precurosrs have been structured as described above, they can be calcined in an inert atmosphere, such as nitrogen or a noble gas at temperatures of about 350° C to about 600° C for at least about two hours to convert the precursors to the catalysts of the present invention. The inert atmosphere prevents excessive oxidation of the tetravalent vanadium to pentavalent vanadium.

However, for those phosphorus-vanadium-oxygen precursors having a phosphorus to vanadium atom ratio of greater that 1:1, it is preferred to calcine in air at temperatures of about 350° C to about 600° C until about 20 to about 80 atom percent of the vanadium has been oxidized to pentavalent vanadium. If more than 80 percent of the vanadium is oxidized to pentavalent vanadium, usually caued by calcining too long or at too high a temperature, the selectivity of the catalysts and the yield of maleic anhydride decrease markedly. On the other hand, oxidation of less than about 20 atom percent of the vanadium during air calcination does not seem to be more beneficial than calcination does not seem to be more beneficial then calcination in an inert atmosphere. It has been found that calcination at 500° C for about 4 hours is generally sufficient. After the phosphorus-vanadium-oxygen precursors have been calcined to form the phosphorus-vanadium-oxygen catalysts of this invention, the catalysts can be used to convert a saturated hydrocarbon to maleic anhydride. However, the initial yield of maleic anhydride may be low, and if this is the case, the catalysts can be "conditioned" as will occur to those skilled in the art, by passing low concentrations of saturated hydrocarbon in air at slow space velocities through the catalysts for a period of time before production operations begin.

ANALYSIS OF THE CATALYSTS

After the catalysts of the present invention have been used about 16 hours to convert saturated hydrocarbons to maleic anhydride, the catalysts develop certain chemical and physical characteristics that distinguish them from catalysts of the prior art. These characteristics are: (1) the valence state of the vanadium; (2) the porosity of the catalysts; and (3) the x-ray diffraction spectrum of the catalyst.

A substantial amount, i.e., greater than 50 atom percent, of the vanadium in the catalysts of the present invention is in the tetravalent state after the catalysts have been used to prepare maleic anhydride for 16 hours from a mixture of about 1.5 atom percent saturated hydrocarbon, such as butane, at a space velocity of about 1500 cc/cc/hour at a temperature of about 440° C. When the catalysts contain less than about 50 atom percent vanadium in the tetravalent state, the catalyst is too unselective to be used for the oxidation of saturated hydrocarbons to maleic anhydride.

The atom percent tetravalent vanadium (in total vanadium) is determined by the "tetravalent vanadium test." In this test, a sample of the catalyst is dissolved in dilute sulfuric acid, and thereafter, the tetravalent vanadium is titrated with a standardized permanganate solution is a first titration. The pentavalent vanadium is then reduced to the tetravalent state by the addition of sodium sulfite and the vanadium is titrated with the standardized permanganate solution in a second titration. The percent tetravalent vanadium can be calculated by dividing the number of milliliters of standardized permanganate solution from the first titration by the number of milliliters of standardized permanganate solution from the second titration, and multiplying the quotient by 100 to obtain a percentage figure.

It has been found that there is a correlation between the porosity of the percent catalysts and the yield of maleic anhydride. As used herein, porosity is the ratio of the volume of interstices of the catalyst to the volume of the catalyst mass.

The porosity of the catalyst made by the present method is determined after they have been used to prepare maleic anhydride for 16 hours from a mixture of about 1.5 atom percent saturated hydrocarbon at a space velocity of about 1500 cc/cc/hour at a temperature of about 440° C. The porosity is calculated from mesurements using a mercury penetrometer, by a method described below, and this method is referred to hereinafter as the porosity test. In this test a pure catalyst sample, i.e., a phosphorus-vanadium-oxygen catalyst without the presence of a carrier, inert diluent or filler, is used. The catalyst sample is weighed, and the apparent density (as g/cc) is determined by measuring the volume occupied by the catalyst sample using mercury displacement at normal atmospheric pressure. Thereafter, the pore volume (as cc/g) is determined by measuring the amount of mercury that is forced into the interstices of the sample at 15,000 pounds per square inch (psi) pressure. Porosity is then calculated by obtaining the product of the apparent density and the pore volume of the catalyst as measured under 15,000 psi mercury pressure. The product is multiplied by 100 to obtain a percentage figure for the porosity.

It has been found that phosphorus-vanadium-oxygen catalysts having a porosity, as measured by the above described porosity test, of less than 35 percent will convert a saturated hydrocarbon, such as butane, to maleic anhydride at 300° to 600° C but the yield is quite low. On the other hand, catalysts having a porosity of at least 35 percent will convert a saturated hydrocarbon to maleic anhydride in good yields. However, it should be noted that catalysts having a porosity of greater than about 65 percent do not give greater yields than catalysts having porosities between about 35 and about 65 percent, and indeed, the yield at high space velocities tends to drop with catalysts above about 65 percent porosity. It is preferred to use catalysts having a porosity between about 40 percent and about 60 percent.

It has also been found that the catalysts of this invention having a phosphorus to vanadium atom ratio between about 1:2 and 2:1 exhibit an X-ray diffraction pattern that is characteristic of the active catalyst after it has been used about 16 hours to convert saturated hydrocarbons to maleic anhydride. The catalysts of this invention have peaks comprising:

| °2 theta (CuKo) | Intensity* | d-spacing |
|---|---|---|
| 14.1 | W | 6.3 |
| 15.7 | W | 5.7 |
| 18.5 | W | 4.80 |
| 23.0 | VS | 3.87 |
| 28.4 | S | 3.14 |
| 29.9 | M | 2.98 |
| 33.7 | W | 2.66 |
| 26.9 | W | 2.44 |

*W = weak; VS = very strong; S = strong; M = medium.

PREPARATION OF MALEIC ANHYDRIDE

The catalysts of the present invention are useful in a variety of reactors to convert saturated hydrocarbons to maleic anhydride. Both fluidized bed reactors and fixed tube heat exchanger type reactors are satisfactory, and details of the operation of such reactors are well known to those skilled in the art. The reaction to convert saturated hydrocarbons to maleic anhydride requires only passing the saturated hydrocarbons admixed with a free oxygen-containing gas, such as air or oxygen enriched air, through the catalysts at elevated temperatures. The saturated hydrocarbons are passed through the catalyst at a concentration of about 1.5 to about 10 volume percent saturated hydrocarbons at a space velocity of about 100 to 4000 cc/cc/hour to provide maleic anhydride yields of greater than 40 percent at temperatures between about 350° C and 600° C.

In the preferred embodiment the catalysts of the present invention are particularly useful in fixed tube heat exchanger type reactors. The tubes of such reactors can vary in diameter from about ¼ inch to about 1.5 inch and the length can vary from about 6 inches to about 10 more feet. It is desirable to have the surfaces of the reactors at a relatively constant temperature and some medium to conduct heat from the reactors is necessary to aid temperature control. Such media can be Woods metals, molten sulfur, mercury, molten lead and the like, or eutectic salt baths. A metal block reactor whereby the metal surrounding the tube acts as a temperature regulating body can also be used. The reactor or reaction tubes can be iron, stainless steel, carbon steel, glass and the like.

Maleic anhydride produced by using the catalysts of this invention can be recovered by any number of means well known to those skilled in the art. For example, the maleic anhydride can be recovered by direct condensation or by absorption in suitable media with subsequent separation and purification of the anhydride.

The pressure in the reactor is not generally critical; therefore, the reaction can be atmospheric, superatmospheric and subatmospheric pressure, although superatmospheric pressure is usually employed.

A larger number of saturated hydrocarbons having from 4 to 10 carbon atoms can be converted to maleic anhydride using the catalysts of the present invention. It is only necessary that the hydrocarbon contains not less than four carbon atoms in a straight chain. As an example, the preferred saturated hydrocarbon is butane, but isobutane, which does not contain four carbon atoms in a straight-chain, is not satisfactory for conversion to maleic anhydride although its presence is not harmful. In addition to butane, other saturated hydrocarbons within the scope of this invention include the pentanes, the hexanes, the heptanes, the octanes, the nonanes, the decanes or mixtures of any of these with or without butane. in addition to the above compounds, cyclic compounds such as cyclopentane or cyclohexane are satisfactory feed materials for conversion to maleic anhydride. Also, the feed stocks do not necessarily have to be totally saturated but can be technical grade hydrocarbons containing up to about 25 weight percent of olefinically unsaturated hydrocarbons, or other hydrocarbon fractions.

The principal product from the oxidation of the above feed materials is maleic anhydride. It should be noted that small amounts of citraconic anhydride may also be produced when the feed stock is a saturated hydrocarbon containing more than 4 carbon atoms.

DESCRIPTION OF THE PREFERRED EMBODIMENTS

This invention is further illustrated by, but not limited to, the following examples:

EXAMPLE I

This example illustrates the results obtained by calcining the catalyst before it is pelletized.

A phosphorus-vanadium-oxygen catalyst was prepared by dissolving vanadium pentoxide in 12 normal hydrochloric acid with stirring and adding sufficient phosphoric acid to the mixture to provide a phosphorus to vanadium ratio of 1.06:1. The solution was heated at reflux conditions, until the solution turned blue. Analysis of an aliquot of the solution by permanganate titration revealed that greater than 90 atom percent of the vanadium was in the tetravalent state. The resultant phosphorus-vanadium-oxygen precursor was recovered by heating the solution to dryness. Then, the precursor was heated to a temperature of about 400° C. for a period of 2 to 4 hours to from a phosphorus-vanadium-oxygen catalyst. The catalyst was then ground to pass a 20 mesh screen, and using 2 weight percent graphite as a pelletizing lubricant, the ground catalyst was pressed into 3/16-inch diameter tablets.

The tablets were charged to a one-inch internal diameter, glass, fixed tube reactor to a depth of about six inches. After 50 hours at about 440° C using a feed containing 1.5 percent butane in air at a space velocity of 1300 cc/cc/hour, maleic anhydride was obtained at a 29 to 33 percent yield. It is believed that the results obtained using this reactor correlate well with the results that would be obtained in a production reactor.

Thereafter, samples of the catalyst were analyzed by the vanadium valence test, the porosity test and the X-ray diffraction test described above. The porosity of the catalyst made by the procedure of this example was about 30 percent. The amount of tetravalent vanadium in total vanadium as measured by the vanadium valence test described above was about 49 atom percent. X-ray diffraction analysis by the X-ray diffraction test as described above using CuKα radiation in a General Electric X-ray diffractometer, Model 5, revealed the presence of a number of crystalline compounds. The X-ray diffraction pattern at °2 theta is shown below:

| °2 theta |
|---|
| 11.8 (M) |
| 14.1 (M) |
| 15.8 (W) |
| 18.5 (M) |
| 21.3 (W) |
| 20.8 (W) |
| 22.4 (M) |
| 22.9 (S) |
| 28.4 (S) |
| 28.9 (S) |

EXAMPLE II

This example illustrates the improved results obtained when using a catalyst prepared by the procedure of the present invention.

The catalyst was prepared as in Example I except that instead of drying the catalyst then calcining at 400° C for 2 to 4 hours and then tabletting, the excess water was evaported, and the remaining solid precursor was then slurried with about 20 weight percent water to form a viscous putty. The putty was then extruded through a die to produce an extrusion of about 3/16-inch diameter, which was then cut to form cylinders about 174-inch long. After these cylinders were allowed to air-dry, they were then calcined at about 500° C for 2 to 4 hours, and charged to a maleic anhydride reactor as in Example I. Under the same conditions used in Example I, the maleic anhydride yield was 43 percent.

Samples of the catalyst made by the procedure of this Example were analyzed by the vanadium valence test, the porosity test and the X-ray diffraction test described above. More than 90 atom percent of the vanadium was tetravalent vanadium as measured by the vanadium valence test. The porosity, as measured by the porosity test, was about 52 percent. X-ray diffraction analysis by the X-ray diffraction test revealed that the catalyst had a characteristic X-ray diffraction pattern at °2 theta using CuKα radiation in a General Electric X-ray diffractometer, Model 5, as follows:

| °2 theta |
|---|
| 14.2 |
| 15.4 |
| 18.5 |
| 22.8 |
| 28.2 |
| 29.7 |
| 33.5 |

EXAMPLES III – IX

The general procedures of Example II was repeated in each of the following examples except that the catalysts were used to fill 2-foot, 4-foot and 11-foot long convertor tubes, each having 1-inch diameters. In all cases, the catalysts, after converting butane to maleic anhydride for at least 16 hours using 1.5 mole percent butane in air at a space velocity of about 1300 cc/cc/hour at about 440° C, contain greater than 75 atom percent tetravalent vanadium in total vanadium as determined by the tetravalent vanadium test, and have the characteristic X-ray diffraction patterns of the catalyst of Example II. In the following tabulation, the porosity as measured by the porosity test is listed for each example. The yield after 50 hours of operation, converter tube length and phosphorus to vanadium atom ratio is also given:

| Example | P/V Atom Ratio | Converter tube length (feet) | Yield (%) | Porosity (%) |
|---------|----------------|------------------------------|-----------|--------------|
| III     | 1.05:1         | 4                            | 50.2      | 54           |
| IV      | 1.05:1         | 11                           | 46.7      | 50           |
| V       | 1.05:1         | 2                            | 48.7      | 52           |
| VI      | 1.05:1         | 11                           | 47.4      | 54           |
| VII     | 1.05:1         | 4                            | 46.0      | 52           |
| VIII    | 1.10:1         | 11                           | 42.9      | 53           |
| IX      | 1.05:1         | 11                           | 42.8      | 49           |

Thus, it can be seen that improved phosphorus-vanadium-oxygen catalysts have been found, and that these catalysts provide improved conversion of saturated hydrocarbons to maleic anhydride. Furthermore, this invention not only contemplates an improved method of preparing a phosphorus-vanadium-oxygen catalyst, but also a process of producing maleic anhydride which comprises passing saturated aliphatic hydrocarbons, such as butane, at a temperature varying from about 350° C to 600° C through a phosphorus-vanadium-oxygen catalyst prepared by a method comprising the steps of reacting the vanadium and phosphorus compounds to form a precursor, making a putty from the precursor, forming a structure from the putty, and calcining the structured precursor.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. As an example, the catalysts may be dried, ground, tabletted, and then calcined to produce improved catalysts. Further, additives, other metals or carriers may be added to the catalysts to improve yields, or additives may be added to the putty to aid in the extrusion. Accordingly, modifications are contemplated which can be made without departing from the spirit of the described invention.

What is claimed is:

1. A method for the preparation of maleic anhydride which comprises passing saturated hydrocarbons containing 4 to 10 carbon atoms, having at least 4 carbon atoms in a straight chain, at temperatures of from about 350° C. to about 600° C. through a phosphorus-vanadium-oxygen catalyst having a phosphorus to vanadium atom ratio in the range of about 1:2 to 2:1, the catalyst having a porosity of at least about 35% as measured by the apparent density of said catalyst (in gm/cc) as determined by mercury displacement at standard atmospheric pressure, multiplied by the pore volume of said catalyst (in cc/gm) determined by volume of mercury forced into pores of said catalyst under a pressure of 15,000 pounds per square inch, prepared by the steps which comprise:

(A) contacting vanadium and phosphorus compounds under conditions which will provide a catalyst precursor wherein greater than 50 atom percent of the vanadium is tetravalent vanadium;
   (B) recovering the catalyst precursor;
   (C) forming the catalyst precursor into structures; and
   (D) calcining the catalyst precursors.

2. A method of claim 1 wherein the catalyst has a phosphorus to vanadium atom ratio in the range of about 1:1 to about 1.2:1.

3. A method of claim 1 wherein the hydrocarbon is n-butane.

* * * * *

UNITED STATES PATENT AND TRADEMARK OFFICE
CERTIFICATE OF CORRECTION

PATENT NO. : 4,111,963
DATED : September 5, 1978
INVENTOR(S) : Ramon A. Mount, Harold Raffelson It is certified that error appears in the above-identified patent and that said Letters Patent are hereby corrected as shown below:

Column 3, line 50, "ratio to about" should read:
 --ratio of about --.

Column 4, line 52, "caued" should read: --caused--.

Column 4, lines 57-58, delete "does not seem to be more beneficial then calcination".

Column 5, line 29, "is a first titration", should read:
 --in a first titration--.

Column 5, line 40, "percent" should read: --present--.

Column 5, line 50, "mesurements" should read:
 --measurements--.

Column 6, line 55, add --or-- after "to about 10".

Column 7, line 8, "larger" should read: --large--.

UNITED STATES PATENT AND TRADEMARK OFFICE
CERTIFICATE OF CORRECTION

PATENT NO. : 4,111,963

DATED : September 5, 1978

INVENTOR(S) : Ramon A. Mount, Harold Raffelson

It is certified that error appears in the above-identified patent and that said Letters Patent are hereby corrected as shown below:

Column 8, line 33, "evaported" should read: --evaporated--.

Column 8, line 38, "174-inch" should read: --1/4 inch--.

Signed and Sealed this

Fourteenth Day of August 1979

[SEAL]

Attest:

LUTRELLE F. PARKER
*Attesting Officer*  *Acting Commissioner of Patents and Trademarks*